United States Patent [19]

Buckwald et al.

[11] Patent Number: 4,564,761

[45] Date of Patent: Jan. 14, 1986

[54] METHOD AND APPARATUS FOR THE ENHANCED DETECTION OF A COMPONENT OF A MATERIAL

[75] Inventors: Robert A. Buckwald, Ramat Yishai; Dario Cabib, Migdal Haemek; Kurt Weiser, Haifa, all of Israel

[73] Assignee: C.I. Ltd., Ramat Yishai, Israel

[21] Appl. No.: 469,159

[22] Filed: Feb. 24, 1983

[30] Foreign Application Priority Data

Mar. 5, 1982 [IL] Israel .................................. 65176

[51] Int. Cl.$^4$ .............................................. G01T 21/71
[52] U.S. Cl. ...................................... 250/341; 250/342; 250/358.1
[58] Field of Search ............... 250/341, 339, 338, 342, 250/340, 358.1; 356/318; 374/5, 9, 45

[56] References Cited

U.S. PATENT DOCUMENTS

| | | | |
|---|---|---|---|
| 3,109,932 | 11/1963 | Spitzer | 250/341 |
| 3,206,603 | 9/1965 | Mauro | 250/341 |
| 3,808,439 | 4/1974 | Renius | 250/341 |
| 4,220,414 | 9/1980 | Barringer | 356/36 |
| 4,306,151 | 12/1981 | Chase | 250/341 |

FOREIGN PATENT DOCUMENTS 154648 11/1981 Japan ................................... 250/339

OTHER PUBLICATIONS

White et al., "Observation of Carrier Densities, in Silicon Devices by Infrared Emission", J. Phys. E. Sci. Instru., 10, p. 817, 1977.

Primary Examiner—Alfred E. Smith
Assistant Examiner—Carolyn E. Fields
Attorney, Agent, or Firm—Benjamin J. Barish

[57] ABSTRACT

A method and apparatus for the enhanced detection of a component in the base material of a sample, particularly of a semiconducting base material having traces of at least one dopant therein to be detected, involves exposing a restricted region of the sample to an intense source of photons to heat the region of the sample sufficiently to cause it to emit infrared radiation therefrom by subjecting the region to electromagnetic radiation, particularly in the form of a laser beam, having a wavelength selected so as to be absorbed by the component to an appreciably larger extent than by the base material, and detecting, by an infrared detector, the infrared radiation emitted by the respective region of the sample as a result of the heating of the component therein produced by the exposure to the electromagnetic radiation.

24 Claims, 3 Drawing Figures

METHOD AND APPARATUS FOR THE ENHANCED DETECTION OF A COMPONENT OF A MATERIAL

FIELD OF THE INVENTION

The present invention relates to a testing method and apparatus, and particularly, to a method and apparatus for the enhanced detection of a component of a material. The invention is applicable to the general problem of measuring small quantities of a substance in a material, but is especially useful for the detection of fine traces of impurities or dopants in semiconducting materials such as silicon devices, and is therefore described below with respect to such an application.

The electrical properties of semiconductor devices depend to a critical degree on the concentration of the impurities or dopants and their spatial distribution. Many techniques have been devised to measure the concentrations of the impurities. One known method, based on Planck's Law, measures the self-emission produced by the impurity when heated; e.g., see J. C. White and J. G. Smith, *J. of Physics E. Sci. Instr.* 10, 817 (1977).

The present invention is directed particularly to the latter type of method, and provides for the enhanced self-emission from the component to be detected which enables its concentration in the base material to be more critically detected and measured.

BRIEF SUMMARY OF THE INVENTION

According to one broad aspect of the present invention, there is provided a method for the enhanced detection of a component in the base material of a sample, characterized by the steps: exposing a restricted region of interest of the sample to an intense source of photons to heat said region of the the sample sufficiently to cause it to emit infrared radiation therefrom by subjecting the said region to electromagnetic radiation having a wavelength selected so as to be absorbed by the component to an appreciably larger extent than by the base material; and detecting the infrared radiation emitted by said region of the sample as a result of the heating of said component therein produced by said exposure.

In the preferred embodiments of the invention described below, the region of interest of the sample is exposed to laser radiation of a wavelength such as to be absorbed by the component to an appreciably larger extent than by the base material, the infrared (IR) radiation emitted by the component, as a result of the heating thereof, being detected. For example, when the sample is a silicon semiconductor, having traces of a dopant whose concentration is to be detected, particularly good results have been produced when the sample is exposed to a carbon dioxide laser having a wavelength of 10.6 micrometers since the absorbance by silicon of the radiation at this wavelength is extremely low compared to the absorbance by the dopant at this wavelength. As a result, the self-emission of the dopant is substantially enhanced, thereby enabling its concentration to be detected and measured with extreme precision.

The invention also provides novel apparatus for the enhanced detection of a substance in accordance with the above method.

It is believed that the invention, and the advantages produced by it, will be better understood by the following discussion of the basic principles on which the invention is based.

BASIC PRINCIPLES ON WHICH INVENTION IS BASED

As well-known (e.g., see *The Infrared Handbook*, W. L. Wolfe and G. J. Zissis, ERIM, 1978, p. 3-14, p. 1-30, p. 1-15, p. 1-29), an object at temperature T emits radiation according to Planck's Law:

$$W_\lambda = \epsilon_\lambda P(\lambda, T) \qquad \text{Eq. (1)}$$

where P is the Planck function at wavelength $\lambda$ and temperature T; $W_\lambda$ is the emitted radiation; and $\epsilon_\lambda$ is emissivity of the material at $\lambda$. Most of the radiation of objects at temperatures below 600° C. is in the region 3 to 15 micrometers; since $\epsilon_\lambda \leq 1$ for any object, the maximum radiation at T is achieved for $\epsilon_\lambda = 1$, the emissivity of the black-body. The absorbance of the material $a_\lambda$ is related to the reflectivity and the transmittance of the material by the following law, $$\rho_\lambda a_\lambda + \tau_\lambda = 1 \qquad \text{Eq. (2)}$$

which is the law of conservation of energy. According to Kirchoff's Law:

$$a_\lambda = \epsilon_\lambda \qquad \text{Eq. (3)}$$

which expresses the fact that the more an object is able to absorb, the more it is able to emit.

Measurements of the above quantities as function of wavelength are widespread in material analysis in chemistry, physics, biology, etc. because the above functions strongly characterize different atoms and molecules in the crystalline, liquid and gaseous forms. A method of analysis called Photo Thermal Radiometery (PTR), and based on the heating of the sample with visible light and subsequent detection of the emitted IR radiation focused or not focused, has been used for biological studies of leaves.

Spectral reflectance and transmittance measurements of silicon material have been recently performed (e.g., see H. H. Wagner and R. R. Schaefer, *J. Appl. Phys.* 50, 2697, 1979) and correlated with concentrations of impurities therein. Pure silicon has a high absorbance in the visible region and a very small absorbance at wavelengths above ~1 micrometer (e.g., see W. Runyan, *Silicon Semiconductor Technology*, McGraw-Hill, 1965, Chapter 9). However, the electrons which are present at room temperature in the conduction band due to the presence of impurities, are strongly absorbing above ~1 micron. The absorbance of these electrons is proportional to their concentration and therefore to the concentration of the impurities. Thus, when silicon material is heated, the radiation emitted by it will be proportional to the impurities present in it, because pure silicon itself has very low emissivity (low absorbance).

As reported in J. C. White and J. G. Smith, ibid., experiments of infrared detection of impurities have recently been carried out by heating a silicon sample. In these experiments, a large silicon sample was heated to a uniform temperature of 100° C., and the emitted radiation was then observed microscopically as function of position. Spatial variations of impurity concentrations were detected across junctions, with spatial resolutions of the order of ten microns.

BASIC ADVANTAGES OF THE INVENTION

By selecting the incident radiation in accordance with the present invention such that the base material (e.g., silicon semiconductor) does not absorb appreciably at the selected wavelength, while the component (e.g., dopant in the silicon semiconductor) does absorb appreciably, the detection of the component is greatly enhanced. In fact, the signal at the detector output is not simply proportional to the concentration of the impurity, but rather it is at least a square function of it, giving rise to an unusually high sensitivity in the detection of the impurity concentration.

In order to illustrate this point, it is to be noted that the temperature of heating T in steady state conditions is given by the following formula (e.g., see H. S. Carslaw and J. C. Jaeger, *Conduction of Heat in Solids*, Oxford, 1973, p. 231):

$$\Delta T = T - T_{room} = C_1 \frac{\alpha \Phi}{Kr} \qquad \text{Eq. (4)}$$

where $C_1$ = constant
$T_{room}$ = initial temperature of the object
$\alpha$ = absorbance of the material in the wavelength region of the incident radiation
$\phi$ = incident power
$K$ = thermal conductivity of the material
$r$ = radius of the heated region The signal (S9 at the detector is given by $$S = C_2 \epsilon [P(T) - P(T_{room})] \qquad \text{Eq. (5)}$$

By substituting Eq. (4) into Eq. (5), for small $\alpha T$, Eq. (5) becomes $$S = C_2 \epsilon \frac{dP(T)}{dT}\bigg|_{T_{room}} \Delta T = C_1 C_2 \frac{\epsilon \alpha \Phi}{Kr} \frac{dP(T)}{dT}\bigg|_{T_{room}} \qquad \text{Eq. (6)}$$

In our example, the wavelength of the incident radiation is chosen such that the base material (medium) does not absorb appreciably at this wavelength, while the component of interest does absorb appreciably; also, the base material (silicon) is such that this situation is valid in all or part of the infrared region (3–15 microns) where most of the self-emitted radiation is present. Accordingly, $\epsilon$ and $\alpha$ are both proportional to the impurity concentration, and therefore "S" in Eq. (6) is square with it. If $\Delta T$ is not small, this dependence can be even more pronounced. In the example of silicon, it turns out that with $\phi = 5$ W, $r = 10$ micrometers, $\Delta T = 100$ C. $\Delta T$ is therefore of the same order of magnitude of $T_{room}$, and if (5) is approximated by the Stefan-Boltzman Law:

$$\begin{aligned} S &= C_2 \epsilon \sigma (T^4 - T_{room}^4) \\ &= C_2 \sigma \epsilon (\Delta T^4 + 4 \Delta T^3 T_{room} + 6 \Delta T^2 T_{room}^2 + 4 \Delta T \cdot T_{room}^3) \end{aligned} \qquad \text{Eq. (7)}$$

Equation (7) is definitely not linear with respect to $\Delta T$ (given by Eq. (4)). If $\Delta T$ is small, all the terms can be neglected in Eq. (7) except the least one in parenthesis, which is proportional to $\Delta T$. However, for small values of r or K, $\Delta T$ can be so large that the $\Delta T^4$ dominates eventually, and S can be proportional to the fifth power of the impurity concentration:

$$S = C_1 C_2 \sigma \epsilon \alpha^4 \left( \frac{\Phi}{Kr} \right)^4 \qquad \text{Eq. (8)}$$

In silicon material, the value of "r" at which this happens is of the order of a few tenths of microns.

If the component of interest is confined to a selected region of the sample, for example a thin film on a weakly absorbing medium, the photon radiation should be focused on the region of interest. This will minimize the heating of the base material and thereby minimize its effects on the output signal (S). The larger the numerical aperture of the optical system, the smaller the region of observation.

The foregoing features and advantages, as well as further features and advantages of the invention, will be more readily apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
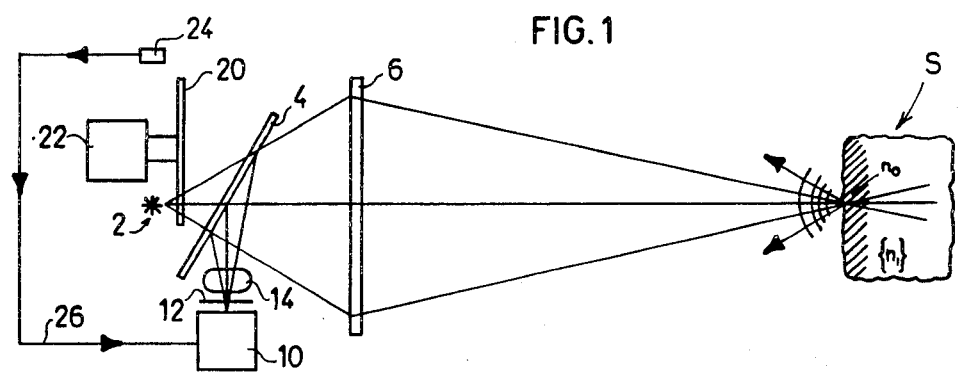
FIG. 1 schematically illustrates an apparatus constructed in accordance with the invention.

With reference first to FIG. 1, there is illustrated a sample S having a region of interest to be examined so as to determine the presence and concentration of a component thereof indicated as "$n_o$", in a base material, indicated as "$n_1$". As an example, the sample S may be a silicon base material ($n_1$) having one or more dopants ($n_o$) or other impurities to be detected.

For this purpose, the apparatus includes an intense photon source, generally designated 2, exposing a region of the sample to electromagnetic radiation. In this example, the intense photon source 2 is a laser which projects the laser beam through a beam-splitter 4 and a focusing optical system 6 focusing the laser beam onto the region of the sample S to be examined. The examined region of the sample is heated by the laser beam and emits infrared radiation which is focused back through the optical system 6 to impinge the beam-splitter 4, the beam-splitter reflecting the emitted infrared radiation to an infrared detector 10.

In front of the detector 10 there is provided a filter and/or window, generally designated 12, of limited wavelength response, namely, of the region of response of the infrared detector 10, in order to make the detector insensitive to the wavelength of the photon source 2. In addition, a dispersive element, generally designated 14, is preferably provided just in front of the infrared detector 10 to define spectral regions facilitating the identification of the detected impurity or impurities. Possible dispersive elements are circular variable filters (CVF), diffraction gratings, and the like.

Preferably, the intense photon source 2 is a laser emitting a laser beam of the selected wavelength. A laser is particularly useful for this purpose since it easily permits focusing a large amount of radiation onto a small spot because of the small angle of divergence of its radiation; moreover, the laser is generally more stable and intense than other photon sources. When the sample S being examined is a silicon semiconductor wafer, particularly good results have been obtained by using a carbon dioxide laser having a wavelength of 10.6 micrometers.

As shown above, the signal outputted by the infrared detector 10 is not simply proportional to the concentration of the component (impurities $n_o$) being detected, but is at least a square function of it, giving rise to an unusually high sensitivity in the detection of the impurity concentration.

In order to further increase the sensitivity of the system, the sample S is exposed to intermittent pulses of radiation from the photon source 2, and the radiation emitted by the sample is measured in synchronism with the intermittent radiation pulses. For this purpose, a chopper disc 20 is located between the photon source 2 and the beam-splitter 4 and is rotated by a chopper drive 22. A synchronous signal detector 24 senses the rotation of the chopper disc 20 and generates synchronising pulses which are fed, via line 26, to the infrared detector 10, thereby synchronising the operation of the detector measuring system with the transmission of the pulses from the photon source.

Figure 2:
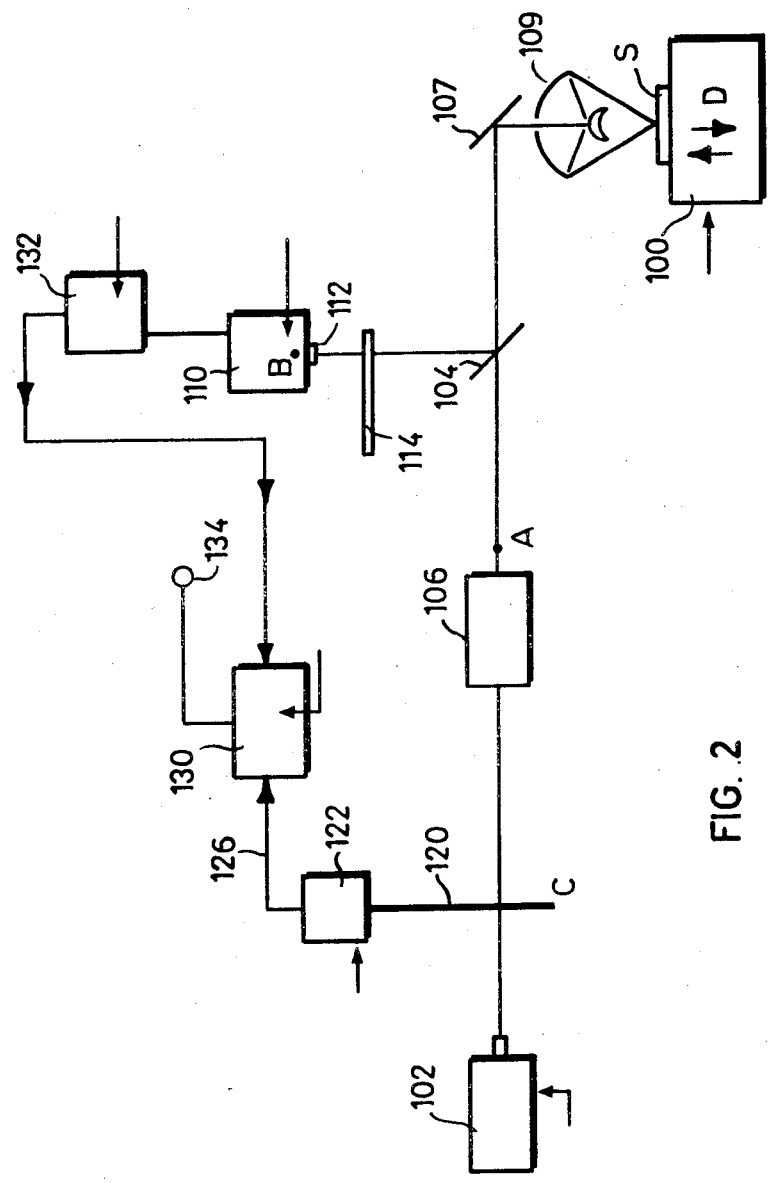
FIG. 2 illustrates an implementation of the apparatus of FIG. 1 in accordance with the present invention.

FIG. 2 illustrates one implementation of an apparatus constructed in accordance with the present invention, for the enhanced detection of a dopant or other impurity trace in a silicon semiconductor base material S. The sample to be examined is placed on a supporting member 100 in the form of a microscope stage. In the apparatus illustrated in FIG. 2, the intense photon source 2 in FIG. 1 is in the form of a carbon dioxide laser 102 of a wavelength of 10.6 micrometers. The laser beam is projected through an optical system including a beam-splitter 104, the radiation emitted by the sample being reflected by the beam-splitter 104 to the infrared detector 110.

The optical system in FIG. 2 further includes a lens system 106 for focusing the laser beam to a fine spot at point A. The laser beam then passes through the beam-splitter 104 and is reflected by a mirror 107 through a microscope reflecting objective 109 which refocuses it onto the surface of sample S on microscope stage 100. The infrared radiation emitted by the sample surface as a result of heating by the laser beam is focused by the microscope objective 109 to a spot at point B of the infrared detector 110, the infrared radiation being reflected by mirror 107 and beam-splitter 104 to the infrared detector 110. The focal point B in the infrared detector 110 of the focused emitted infrared radiation is conjugate to the focal point A of the laser beam.

The infrared detector 110 is preferably a liquid-nitrogen-cooled InSb detector including a sapphire window 112 which absorbs laser radiation and transmits the emitted infrared radiation, to thereby make the detector sensitive only to the emitted infrared radiation. In addition, a circular variable filter 114 is optionally included in front of the detector window 112, serving as a dispersive element to define spectral regions in order to permit identification of the detected impurity or impurities in the examined sample S.

It will be noted that in the system illustrated in FIG. 2, the optical system uses reflecting elements so that the focal point and transmission characteristics of the optics will be nearly independent of wavelength.

The system of FIG. 2 also includes a synchronous detection arrangement to increase the sensitivity and stability of the measurement. For this purpose, a chopper disc 120 is provided in front of the laser 102 for chopping the continuous wave laser beam produced by the laser into intermittent pulses before entering the optical system including the focusing lenses 106 and beam-splitter 104. Chopper disc 120 is driven by a chopper drive 122, the chopper further producing synchronising pulses fed via electrical conductor 126 to a lock-in amplifier 130. The latter amplifier receives the output signals from the infrared detector 110, after amplification in pre-amplifier 132. The operation of the lock-in amplifier 130 is thereby synchronised by the chopper synchronising pulses, as known in synchronous detection systems, to produce an analog output at the output terminal 134 which is relatively independent of room temperature drifts and stray radiation.

Preferably, the microscope objective 109 is provided with a large numerical aperture in order to concentrate the same amount of radiation on a smaller amount of absorbing material, and thereby to increase the heating of the sample, when required for sufficient signal strength. A high numerical aperture in order to heat small spots is particularly desirable when using the above-described synchronous detection technique because the smaller the heated spot, the shorter is the diffusion time of the heat. In addition, a large numerical aperture, by decreasing the volume being heated, also decreases the amount of the base material ($n_1$) being heated, thereby increasing the sensitivity of the infrared detector to the component ($n_o$) of interest. Further, a large numerical aperture allows probing a sample at different depths when all the components are weakly absorbing.

The chopping by chopper 120 is preferably performed at low frequencies compared to the characteristic frequency of the infrared heat waves propogated in the sample, so that the heated region on the sample has enough time to cool back down to room temperature before it is heated again.

As one example, the optical system may have a large numerical aperture of 0.65, and the chopping frequency may be 250 Hz.

By utilizing coaxial optics for the photon source (e.g. laser 102) and the infrared detection system, the system of FIG. 2 provides a low-cost arrangement which is simpler to align and which can more easily probe small regions.

While the invention has been described with respect to certain preferred embodiments, it will be appreciated that these are set forth purely for purposes of example. For example, while a laser is preferred as the intense source of photons of the selected wavelength, other sources could be used, such as tungsten, xenon or mercury lamps. Further, the selected wavelength can be provided by the use of optical filters or the like. Also, the invention can be used with known scanning arrangements for scanning the article being examined. In addition, the component to be detected may be in the same phase as the body material, or may be embedded or dissolved as a different phase. Thus, in addition to probing of silicon wafers for detecting and measuring the amount of implanted or diffused impurity, the invention may be used in other applications, such as in the analysis of materials (organic and inorganic), crystallography, thin film analysis, optical memories based on reading minute amounts of impurities in silicon, analysis of water on surfaces, impurities in insulators, substances or contaminants on the surface of metal impurities in plastics, composition analysis of biological materials, process control and testing.

Figure 3:
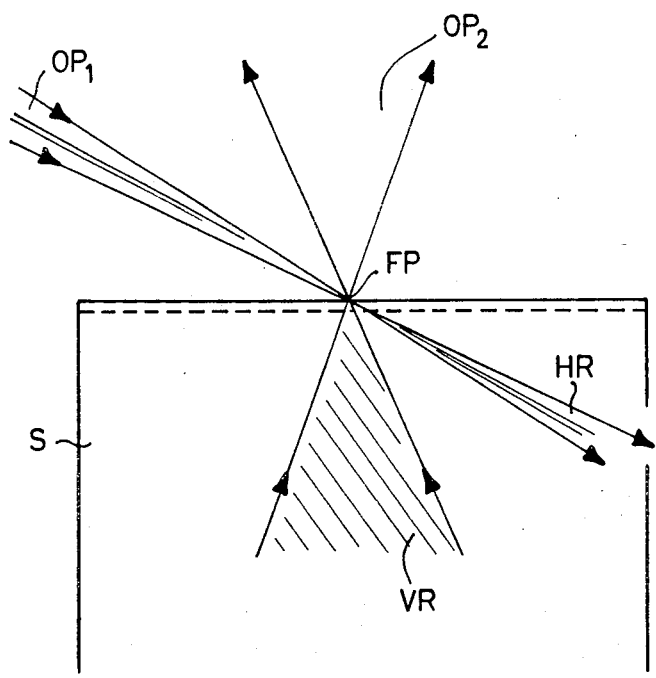
FIG. 3 diagrammatically illustrates another implementation of the invention.

FIG. 3 diagrammatically illustrates another implementation of the invention involving a first path $OP_1$ for the focused light or laser beam, and a second, different path $OP_2$ for the radiation emitted by the component in the sample S, both paths being focused on the same point FP. Such a two-path arrangement has been found to provide a dramatic improvement in the dynamic range of measurements capable of being attained by the method and apparatus of the invention.

Thus, as shown in FIG. 1, optical path $OP_1$ is the path of the focused light or laser beam, and therefore the path for heating the sample S, such as a silicon semiconductor having a dopant or other impurity traces. Optical path $OP_1$ is brought into a focus at point FP on the surface of sample S and is effective to heat the sample within the heating region HR. When the same optical path is used for detecting the infrared radiation emitted by the dopant in the sample, it was found that the heated region HR becomes a source of appreciable background radiation, which adversely affects the dynamic range measurements of the technique.

Accordingly, a different optical path, namely path $OP_2$, also focused at the focal point FP, is used for detecting the emitted radiation, namely the radiation emitted by the dopant or other impurity trace. Thus the region VR is sensed by the infrared detector (110 in FIG. 2), which is different from the region HR heated by the laser beam, the two regions HR and VR being common only at the focal point FP. The detector viewing the heated region along the optical path $OP_2$ is thus prevented from receiving the thermal radiations from the heated region HR of the laser path. Accordingly, this two-path method diagrammatically illustrated in FIG. 3 produces a heated region HR which crosses the viewed or detected region VR at only one point or small region, FP, so that only the heat from this latter point or small region is effectively detected by the infrared detector directed along optical $OP_2$. This has been found to substantially improve the dynamic range of the system thereby making it considerably more useful.

It will be appreciated that this two-path technique may be used in the microscopic mode or in the macroscopic mode, and that other configurations are possible, such as passing through the center and viewing from the side.

The accuracy and dynamic range of the measurement of the impurity concentration in the silicon can be improved considerably by radiating the sample at its Brewster angle, thereby decreasing the amount of energy reflected and increasing the efficiency of the use of the laser energy. If the laser beam is polarized with the electric vector in the plane defined by the beam and the perpendicular to the sample, there is no reflected radiation at all, which is an advantage as far as possible hazards are concerned. In this respect, it is to be noted that many lasers (e.g., many $CO_2$ lasers) inherently produce polarized beams.

Many other variations, modifications and applications of the invention will be apparent.

What is claimed is:

1. A method for the enhanced detection of a component in the base material of a sample, characterized by the steps of:
    exposing a restricted region of interest in the sample to an intense source of photons to heat said region of the sample sufficiently to cause it to emit infrared radiation therefrom by subjecting the said region to electromagnetic radiation having a wavelength selected so as to be absorbed by the component to an appreciably larger extent than by the base material;
    and detecting the infrared radiation emitted by said region of the sample as a result of the heating of said component therein produced by said exposure.

2. The method according to claim 1, wherein said electromagnetic radiation is a laser beam.

3. The method according to claim 1, wherein said emitted radiation is microscopically detected.

4. The method according to claim 1, wherein the electromagnetic radiation is directed towards the sample along one optical path, and the infrared radiation emitted by said component in the sample is directed along a second optical path intersecting said first optical path.

5. The method according to claim 4, wherein said emitted infrared radiation is microscopically detected.

6. The method according to claim 1, wherein said region of interest is exposed to intermittent pulses of radiation, and the detection of the emitted infrared radiation is controlled in synchronism with said intermittent pulses.

7. The method according to claim 1, wherein the sample is of a semiconducting base material having traces of at least one dopant therein to be detected.

8. The method according to claim 7, wherein said semiconducting base material is silicon.

9. The method according to claim 7, wherein said electromagnetic radiation is produced by a carbon dioxide laser having a wavelength of 10.6 micrometers.

10. A method for the enhanced detection of a component in the base material of a sample, characterized by the steps:
    exposing a region of interest of the sample to an intense source of photons produced by a laser beam having a wavelength such as to be absorbed by the component to an appreciably larger extent than by the base material;
    and detecting the infrared radiation emitted by said component as a result of the heating thereof produced by the exposure to said laser beam.

11. The method according to claim 10, wherein said laser beam is directed towards the sample along one optical path, and the infrared radiation emitted by said component in the sample is detected along a second optical path intersecting said first optical path in the sample.

12. Apparatus for the enhanced detection of a component in the base material of a sample, characterized in that said apparatus includes:
    a support for the sample;
    a source of electromagnetic radiation comprising means for exposing a restricted region of interest in the sample, when the sample is on said support, to an intense source of photons to heat said region of the sample sufficiently to cause it to emit infrared radiation therefrom by the heating thereof;
    said source of electromagnetic radiation having a wavelength selected so as to be absorbed by the component to an appreciably larger extent than by the base material;
    and infrared detector means for detecting the infrared radiation emitted by said region of the sample as a result of the heating of said component therein produced by the exposure thereof to said electromagnetic radiation source.

13. Apparatus according to claim 12, wherein said electromagnetic radiation source is a laser.

14. Apparatus according to claim 12, wherein said source of electromagnetic radiation is oriented to expose the region of the sample along one optical path, and the detector means is oriented to detect the infrared radiation emitted by said component in the sample along a second optical path intersecting said first optical path in the region of said sample.

15. Apparatus for the enhanced detection of a component in the base material of a sample, characterized in that said apparatus includes:
  a support for the sample;
  a laser for exposing a region of the sample to electromagnetic radiation;
  said laser having a wavelength such that its radiation is absorbed by the component to an appreciably larger extent than by the base material; and
  infrared detector means for detecting the infrared radiation emitted by said component as a result of the heating thereof produced by said laser radiation.

16. Apparatus according to claim 15, wherein said laser is a carbon dioxide laser producing a laser beam of 10.6 micrometer wavelength.

17. Apparatus according to claim 15,
  wherein said infrared detector means includes a window relatively conductive with respect to the emitted infrared radiation, but substantially non-conductive with respect to the laser radiation.

18. Apparatus according to claim 15, further including focusing means having a large numerical aperture for focusing the laser beam on a small region of the sample to maximize heating of the component and to minimize heating of the surrounding base material.

19. Apparatus according to claim 15, further including a microscopic objective means focusing the laser radiation onto a small spot on the sample and focusing the infrared radiation emitted from the sample on the infrared detector means.

20. Apparatus according to claim 15, further including intermittent pulsing means causing said laser beam to be applied to the sample in the form of intermittent pulses, said detector means including a lock-in amplifier amplifying the output of the detector means in synchronism with said intermittent pulsing means.

21. Apparatus according to claim 20, wherein said intermittent pulsing means comprises a chopper between the laser and the sample support.

22. Apparatus according to claim 15, further including a beam-splitter located so as to transmit the laser beam therethrough to the sample on the support, and to reflect the infrared radiation emitted by the sample to the detector means.

23. Apparatus according to claim 15, further including a dispersive element means in front of the detector means defining spectral regions facilitating identification of an impurity or impurities detected.

24. Apparatus according to claim 15, wherein said laser is oriented to expose the region of the sample along one optical path, and the infrared detector is oriented to detect the radiation emitted by said component in the sample along a second optical path intersecting said first optical path within said sample.

* * * * *

UNITED STATES PATENT AND TRADEMARK OFFICE
CERTIFICATE OF CORRECTION

PATENT NO.  :  4,564,761

DATED        :  January 14, 1986

INVENTOR(S) :  Robert A. Buckwald, Dario Cabib, Kurt Weiser

It is certified that error appears in the above–identified patent and that said Letters Patent are hereby corrected as shown below:

Column 2, line 17, change "$\varepsilon \lambda \leq 1$" to -- $\varepsilon\lambda \leq 1$ ;

Column 2, line 24, change "$P\lambda a\lambda + T\lambda = 1$" to -- $P\lambda + a\lambda + T\lambda = 1$ Column 3, line 35, change "small $\alpha T$" to -- small $\Delta T$ Column 3, line 64, change "least" to -- last

[SEAL]

Signed and Sealed this

Seventeenth Day of June 1986

Attest:

DONALD J. QUIGG

Attesting Officer

Commissioner of Patents and Trademarks